United States Patent [19]

Hermeling et al.

[11] Patent Number: 5,151,548
[45] Date of Patent: Sep. 29, 1992

[54] BENZYL ALCOHOLS AND THEIR LOWER ALKANECARBOXYLIC ACID ESTERS

[75] Inventors: Dieter Hermeling, Neustadt; Dieter Degner, Dannstadt-Schauernheim; Albrecht Harreus, Ludwigshafen; Norbert Goetz, Worms; Jochen Wild, Deidesheim; Hans Theobald, Limburgerhof; Bernd Wolf, Mutterstadt, all of Fed. Rep. of Germany

[73] Assignee: BASF Aktiengesellschaft, Ludwigshafen, Fed. Rep. of Germany

[21] Appl. No.: 365,129

[22] Filed: Jun. 12, 1989

[30] Foreign Application Priority Data

Jun. 21, 1988 [DE] Fed. Rep. of Germany ....... 3820897

[51] Int. Cl.$^5$ ................. C07C 33/50; C07C 69/07; C07C 69/157; C07C 69/24
[52] U.S. Cl. .................................. 560/255; 204/59 F; 204/59 R; 204/72; 204/78; 560/254; 568/807; 568/812
[58] Field of Search ................ 560/254, 255; 568/812, 568/807

[56] References Cited

U.S. PATENT DOCUMENTS

| | | | |
|---|---|---|---|
| 3,029,290 | 4/1962 | Lindemann et al. | 560/254 |
| 3,448,021 | 6/1969 | Koehl | 204/72 |
| 4,429,153 | 1/1984 | Punja | 562/493 |

FOREIGN PATENT DOCUMENTS 21495 7/1970 Japan .................................. 568/812

OTHER PUBLICATIONS

Acta Chem. Scand. B 32 (1978), 157.
Acta Chem. Scand. B 33 (1979), 113.
J. Org. Chem. 51 (1986), 4544

*Primary Examiner*—Vivian Garner
*Attorney, Agent, or Firm*—Keil & Weinkauf

[57] ABSTRACT

Benzene derivatives of the general formula

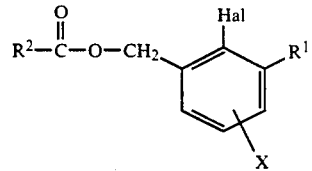

where Hal is halogen, $R^1$ is a hydrocarbon radical of 1 to 18 carbon atoms, $R^2$ is hydrogen or alkyl of 1 to 6 carbon atoms and X is hydrogen or halogen, are prepared by a process in which a toluene derivative of the general formula

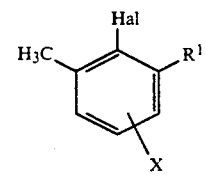

is electrochemically oxidized in the presence of an acid of the formula $R^2$—COOH (III). Novel benzene derivatives of the general formula

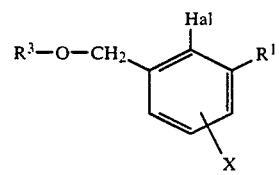

where $R^3$ is hydrogen or an $R^2$—CO— radical but $R^1$ cannot be methyl if X is hydrogen, and of the general formula

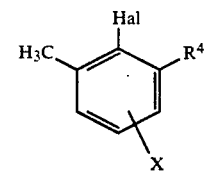

where $R^4$ is a branched or cyclic alkyl radical of 3 to 12 carbon atoms, but $R^4$ cannot be isopropyl if X is hydrogen. The compounds of formulas IV and VI are intermediates for crop protecting agents, e.g. pyrethroids.

1 Claim, No Drawings

BENZYL ALCOHOLS AND THEIR LOWER ALKANECARBOXYLIC ACID ESTERS

The present invention relates to a novel electrochemical process for the preparation of benzene derivatives, and to novel benzene derivatives. In the novel process, toluene derivatives are converted into benzyl esters, which can be used, for example, for the preparation of benzyl alcohols. The novel benzene derivatives of this invention are benzyl esters, benzyl alcohols and toluene derivatives.

We have found that benzyl esters of the general formula

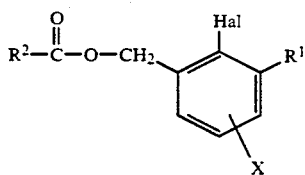

where Hal is halogen, $R^1$ is a straight-chain, branched or cyclic hydrocarbon radical of 1 to 18 carbon atoms, $R^2$ is hydrogen or alkyl of 1 to 6 carbon atoms and X is hydrogen or halogen, can be advantageously prepared by electrochemically oxidizing a toluene derivative of the general formula

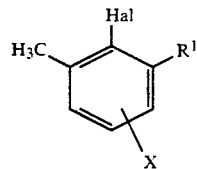

where Hal, $R^1$ and X have the abovementioned meanings, in the presence of an acid of the formula $R^2$—COOH (III).

It is known that benzyl alcohols and their esters with lower alkanecarboxylic acids can be prepared by the processes described in Houben-Weyl, Methoden der Organischen Chemie, for example by a) brominating a methylaromatic with N-bromosuccinimide (cf. Volume 4, 221), reacting the bromination product with a salt of a carboxylic acid and then hydrolyzing the product, b) acetoxylating a methylaromatic with a lead(IV) or cerium(IV) compound or by oxidation with molecular oxygen, c) oxidizing a methylaromatic to give the corresponding benzaldehyde or benzoic acid (E3 and IV/1b, respectively) and then reducing the product to the alcohol, or d) forming an organometallic compound from a halogenated aromatic and then reacting the product with formaldehyde.

For the preparation of the compounds of the formula I, these known methods are either unsuitable or are not very suitable owing to their poor selectivity. For example, the starting materials of the formula II are attacked by the stated oxidizing agents in (a) to (c), both at the methyl group and at the aliphatic radical $R^1$. Starting materials having two halogen atoms also exhibit poor differentiation in the formation of the organometallic intermediate in (d). Thus, reaction mixtures from which the desired compounds of the formula I can only be isolated with difficulty are obtained.

In contrast, the electrochemical process of the invention gives the benzyl esters with high selectivity.

The toluene derivatives of the formula II which are required for the novel process contain, as radical $R^1$, a straight-chain, branched or cyclic hydrocarbon radical of 1 to 18 carbon atoms. Hydrocarbon radicals of this type are, in particular, straight-chain and branched alkyl radicals and cycloalkyl radicals. Examples of straight-chain alkyl radicals are methyl, ethyl, propyl, butyl, pentyl, hexyl, etc. Examples of branched alkyl radicals are those of the formula

which contain a total of not less than 3 carbon atoms and where $R^5$, $R^6$ and $R^7$ are each hydrogen or alkyl of 1 to 6, preferably 1 to 3, carbon atoms. Examples of radicals of this type are isopropyl, tert-butyl, sec-butyl and isobutyl. Cycloalkyl radicals are those which have a cycloalkyl group or a bicycloalkyl group. The cycloalkyl groups contain, for example, 3 to 8 cyclic carbon atoms, which in turn may carry alkyl groups of 1 to 5, preferably 1 to 3, carbon atoms. Examples of cycloalkyl radicals of this type are cyclopropyl, cyclopentyl, cyclohexyl, 3,5-diethylcyclohexyl and tetramethylcyclopropyl. The bicycloalkyl groups contain, for example, 5 to 12 bicyclic carbon atoms, which in turn may contain alkyl groups of 1 to 5, preferably 1 to 3, carbon atoms. Specific examples of bicycloalkyl groups are 2-norbornyl, bicyclo[4.1.0]hept-1-yl and 2,6-dimethylbicyclo[4.1.0]-hept-1-yl.

The halogen atoms present in the toluene derivatives of the formula II are preferably fluorine, chlorine or bromine atoms. The following compounds are examples of toluene derivatives of the formula II: 2-chloro-3-isopropyltoluene, 2-fluoro-3-isopropyltoluene, 2-bromo-3-isopropyltoluene, 2-chloro-3-cyclohexyltoluene, 3-cyclopentyl-2-fluorotoluene, 2-chloro-3-cyclopentyltoluene, 2-chloro-3-tert-butyltoluene, 2-fluoro-3-tert-butyltoluene, 2-chloro-3-sec-butyltoluene and 2-chloro-6-fluoro-3-isopropyltoluene.

The toluene derivatives of the formula II are electrochemically oxidized to their compounds of the formula I in the presence of an alkanoic acid of the formula III, of which formic, acetic and propionic acid are preferred.

The electrochemical oxidation of monosubstituted toluenes is described in, for example, U.S. Pat. No. 3,448,021; Acta Chem. Scand. B 32 (1978), 157; Acta Chem. Scand. B 33 (1979), 113 and J. Org. Chem. 51 (1986), 4544. In comparison, it is surprising that, in the novel process, the toluenes of the formula II which contain further alkyl radicals in addition to the methyl group are smoothly converted into the compounds of the formula I with selective oxidation of the methyl groups.

The electrochemical oxidation can be carried out in a conventional electrolysis cell, undivided flow-through cells being preferably used. Examples of anode materials used are noble metals, such as platinum, and oxides, such as $RuO_2$, $Cr_2O_3$ or $TiOx/RuOx$; graphite is particularly preferably used. Cathode materials can include iron, steel, nickel, noble metals, such as platinum, and graphite. The electrolyte used is a solution of the toluene in the alkanoic acid, to which an auxiliary electrolyte is added to increase the conductivity. Suitable auxiliary electrolytes are the conductive salts conventionally used in electrochemistry, for example fluorides, tetrafluoborates, sulfonates and alkylsulfates. A cosolvent can also be added to increase the solubility of the toluenes. Examples of cosolvents are ketones, such as acetone or methyl ethyl ketone, nitriles, such as acetonitrile or propionitrile, and anhydrides, such as acetic anhydride.

The electrolyte has, for example, the following composition:
1-20% of a toluene of the general formula II
1-10% of a conductive salt
0-20% of a cosolvent and
50-95% of an alkanoic acid.

The current densities and electrolysis temperatures can be varied within wide limits. For example, electrolysis is carried out at 0.2-20 A/dm² and at from 15° to 95° C. The toluenes used can be substantially converted and the discharged electrolysis mixtures are worked up by conventional methods, for example by distillation, extraction and crystallization. The cosolvent, the excess alkanoic acid and the conductive salt can be separated off from the benzyl esters and then recycled to the electrolysis, together with any unconverted toluene of the formula II.

The present invention furthermore relates to the novel benzene derivatives of the general formula

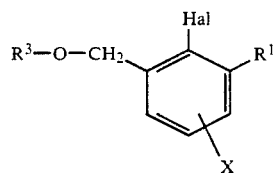

IV where Hal is halogen, $R^1$ is a straight-chain, branched or cyclic hydrocarbon radical of 1 to 18 carbon atoms, $R^3$ is hydrogen or an $R^2$—CO— radical, $R^2$ is hydrogen or alkyl of 1 to 6 carbon atoms and X is hydrogen or halogen, but $R^1$ cannot be methyl if X is hydrogen.

Examples of compounds of this type are the benzene derivatives of the formula IV which are shown in the Table below

| No. | Hal | $R^1$ | $R^3$ | X |
|---|---|---|---|---|
| 1 | Cl | ▷ (cyclopropyl) | CH₃—CO— | H |
| 2 | Cl | —CH(CH₃)—CH₂—CH₃ | CH₃—CO— | H |
| 3 | Br | —CH(CH₃)₂ | H | H |
| 4 | Br | —CH(CH₃)₂ | CH₃—CO— | H |
| 5 | Cl | cyclohexyl | CH₃—CO— | H |
| 6 | Cl | cyclohexyl | H | H |
| 7 | F | —CH(CH₃)₂ | H | H |
| 8 | F | —CH(CH₃)₂ | CH₃—CO— | H |
| 9 | Cl | cyclopentyl | H | H |
| 10 | Cl | cyclopentyl | CH₃—CO— | H |
| 11 | F | cyclopentyl | H | 6-Cl |
| 12 | F | cyclopentyl | CH₃—CO— | 6-Cl |
| 13 | Cl | —CH(CH₃)₂ | CH₃—CO— | H |
| 14 | Cl | —CH(CH₃)₂ | H | H |
| 15 | Cl | —CH(CH₃)₂ | CH₃—CO— | 6-F |
| 16 | Cl | —CH(CH₃)₂ | H | 6-F |
| 17 | Cl | —C(CH₃)₃ | CH₃CO— | H |
| 18 | Cl | —C(CH₃)₃ | H | H |
| 19 | Cl | —CH(CH₃)—CH₂—CH₃ | H | H |
| 20 | F | cyclopentyl | CH₃—CO— | H |
| 21 | F | cyclopentyl | H | H |
| 22 | Cl | —CH(CH₃)₂ | H—CO— | H |
| 23 | Cl | —CH(CH₃)₂ | CH₃—CH₂—CO— | H |
| 24 | F | —C(CH₃)₃ | CH₃—CO— | H |
| 25 | F | —C(CH₃)₃ | H | H |

Of particular industrial interest are the novel benzene derivatives of the general formula

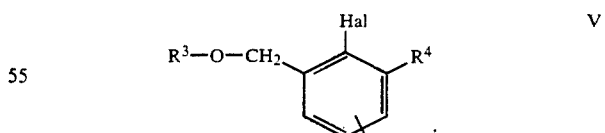

V where Hal is fluorine, chlorine or bromine, $R^4$ is a branched or cyclic alkyl radical of 3 to 12, preferably 3 to 8, carbon atoms, and $R^3$ and X have the abovementioned meanings.

The compounds of the general formulae IV and V are important intermediates for the synthesis of crop protection agents, in particular of novel pyrethroids. In general, the benzyl alcohols of the formula

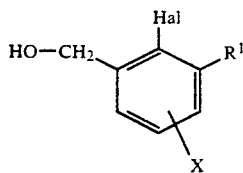

where Hal, $R^1$ and X have the abovementioned meanings, are used as starting materials for this purpose. These benzyl alcohols are obtained from the benzyl esters of the formula IV where $R^3$ is a radical $R^2$—CO— by hydrolysis. Hydrolysis is carried out, for example, by a conventional method. To do so, the relevant benzyl ester in an inert organic solvent, such as tetrahydrofuran, dioxane, ethanol or methanol, is hydrolyzed with a base, such as sodium hydroxide, with or without the addition of water. The acidic hydrolysis of a benzyl ester is carried out, for example, by reaction in one of the above solvents with the addition of water and an acid, for example hydrochloric acid.

The hydrolyses are preferably carried out at from room temperature to the boiling point of the reaction mixtures.

The present invention also relates to the novel benzene derivatives of the general formula

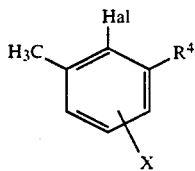

where Hal, $R^4$ and X have the abovementioned meanings but $R^4$ cannot be isopropyl if X is hydrogen.

Compounds of this type, which are used as starting materials for the novel electrochemical oxidation, are described above. These toluenes can be prepared, for example, by exchanging the amino group of 2,6-dialkylated anilines for the halogen atom by diazotization and a Sandmeyer or Balz-Schiemann reaction. The 2,6-dialkylated anilines can be obtained either from the analogous phenols (European Patent 53,696) or by selective orthoalkylation of anilines (U.S. Pat. No. 3,678,113 and German Laid-Open Application DOS 3,309,354).

Another possible method of synthesis for the anilines is the amino Claisen rearrangement reaction (Izv. Akad. Nauk. SSR, Ser. Khim. 1982, 2160 et seq.). The unsaturated anilines obtained are then selectively hydrogenated in the side chain.

EXAMPLE 1

2-Chloro-3-isopropylbenzyl alcohol a) Preparation of 2-chloro-3-isopropyltoluene 224 g (1.5 moles) of 2-isopropyl-6-methylaniline are introduced into 900 ml of half-concentrated hydrochloric acid. A solution of 113.9 g (1.65 moles) of sodium nitrite in 500 ml of water is added dropwise at an internal temperature of from 0° to 5° C. The reaction mixture thus prepared is added a little at a time, at from 0° to 5° C., to a mixture of 298 g (2 moles) of freshly prepared copper(I) chloride and 800 ml of concentrated hydrochloric acid. The temperature of the reaction mixture is allowed to increase to room temperature, and the reaction mixture is further heated at 90° C. until evolution of nitrogen has ceased, in order to complete the reaction. The reaction mixture is then subjected to steam distillation. Extraction with dichloromethane gives 199 g of a crude product which, according to gas chromatographic analysis, consists of 48.3% of 2-chloro-3-isopropyltoluene and 42.2% of 2-isopropyl-6-methylphenol. 30 g (0.75 mole) of sodium methylate are dissolved in 250 ml of methanol, the crude product is added dropwise, stirring is carried out for 3 hours at 50° C., the mixture is evaporated down and toluene is added twice and in each case the mixture is evaporated down. The residue is suspended in cyclohexane and the suspension is filtered over silica gel. Evaporating down the filtrate and distilling the residue give 87 g (34%) of 2-chloro-3-isopropyltoluene (bp. 115°–120° C./15 mbar).

b) Electrolytic synthesis of 2-chloro-3-isopropylbenzyl acetate

The 2-chloro-3-isopropyltoluene obtained according to Paragraph a) is electrolyzed in the electrolysis cell described below, under the stated conditions.

Apparatus: undivided cell having 11 bipolar electrodes
Anode: graphite.
Electrolyte: 186 g (1.104 moles) of 2-chloro-3-isopropyltoluene, 300 g of acetic anhydride, 90 g of $KSO_3C_6H_5$ and 2,424 g of acetic acid.
Cathode: graphite.
Current density: 0.67 A/dm$^2$.
Electrolysis temperature: 70° C.
Electrolysis using 7 F/mole of 2-chloro-3-isopropyltoluene. The electrolyte is pumped through the cell at a rate of 200 l/h during the electrolysis.

When the electrolysis has ended, acetic acid/acetic anhydride are distilled off under atmospheric pressure at up to 150° C. and the residue is partitioned between $H_2O$ and methyl tert-butyl ether. Methyl tert-butyl ether is distilled off from the organic phase under atmospheric pressure. 355 g of a residue, which contains 11.7 g of 2-chloro-3-isopropyltoluene and 165.7 g of 2-chloro-3-isopropylbenzyl acetate according to gas chromatographic analysis, are obtained. This gives a conversion of 93.7%, a yield of 66.3% and a selectivity of 70.7%. 2-Chloro-3-isopropylbenzyl acetate is purified by distillation at 92°–94° C. and under 2 mbar.

$^1$H—NMR (270 MHz, CDCl$_3$).

δ (ppm)=1.25 (d, 6H, —CH(CH$_3$)$_2$); 2.14 (s, 3H, CH$_3$COO—); 3.48 (septet, 1H, —CH(CH$_3$)$_2$; 5.23 (s, 2H, —CH$_2$OAc); 7.28 (m, 3H, aromat.—H).

c) Preparation of 2-chloro-3-isopropylbenzyl alcohol 70 g of the benzyl ester obtained according to Paragraph b) are dissolved in 500 ml of dioxane. 180 g of 8% strength sodium hydroxide solution are added to the solution. The mixture is stirred for 5 hours at 50° C. and evaporated down under reduced pressure, the residue is taken up with water and the aqueous mixture is extracted several times with dichloromethane. 57.0 g (quantitative) of 2-chloro-3-isopropylbenzyl alcohol (bp.=87°–89° C./18 mbar) are obtained from the organic phase after drying and evaporation.

$^1$H—NMR (250 MHz, CDCl$_3$)

δ (ppm)=1.25 (d, 6H, —CH(CH$_3$)$_2$); 2.1 (m, 1H, OH); 3.45 (m, 1H, —CH<); 4.8 (d, 2H, —CH$_2$); 7.2–7.4 (m, 3H, aromat.—H).

EXAMPLE 2

2-Chloro-3-cyclopentylbenzyl alcohol a) Preparation of 2-cyclopentyl-6-methylphenol 170 ml of boron trifluoride/phosphoric acid adduct are added to 1.08 kg (10 moles) of o-cresol in 400 ml of pentane. 680 g (10 moles) of cyclopentene, dissolved in 1 l of pentane, are added dropwise at the reflux temperature in the course of 3 hours. The mixture is stirred for a further hour at the reflux temperature and then poured into ice water. The organic phase is separated off and is extracted with 4 times 600 ml of 10% strength sodium hydroxide solution. The organic phase is dried and evaporated down and the residue is distilled (84°–88° C./0.2 mbar). 515 g of 2-cyclopentyl-6-methylphenol (corresponding to 37% of theory, based on converted cresol) are obtained. 217 g of o-cresol and 282 g of 4-cyclopentyl-2-methylphenol are obtained from the alkaline wash solution after acidification, extraction and distillation.

b) Preparation of 2-cyclopentyl-6-methylcyclohexylamine

In a 5 l stirred autoclave, a mixture of 485 g of 2-cyclopentyl-6-methylphenol and 551 g of ammonia is subjected to reductive amination in the presence of a powder catalyst containing 10% by weight of palladium and 5% by weight of praseodymium oxide on alumina at 230° C. and under a hydrogen pressure of 300 bar until the pressure remains constant. After the catalyst has been separated off, 484 g (95% yield) of crude 2-cyclopentyl-6-methylcyclohexylamine are obtained, and can be used without further purification in the next stage.

c) Preparation of 2-cyclopentyl-6-methylaniline

An extruded catalyst (3 mm diameter, 10 mm length) which contains 0.5% by weight of palladium on a mixture of 19.4% by weight of magnesium oxide and 80.6% by weight of alumina is introduced into a pressure-resistant cylindrical tube having a volume of 0.25 l, as a reactor. The catalyst is heated to 220° C. 60 g/hour of 2-cyclopentyl-6-methylcyclohexylamine are introduced under atmospheric pressure and at the same time a gas mixture consisting of 200 l (S.T.P.)/hour of ammonia and 300 l (S.T.P.)/hour of hydrogen is passed through the reactor by the cocurrent method. As soon as it leaves the reactor, the reaction product is cooled. According to gas chromatographic analysis, it consists of 44% by weight of 2-cyclopentyl-6-methylcyclohexylamine (bp. 132° C./18 mbar) and 54% by weight of 2-cyclopentyl-6-methylaniline (bp.=160° C./18 mbar). These two amines can easily be separated from one another by distillation.

d) Preparation of 2-chloro-3-cyclopentyltoluene 173 g (0.96 mole) of 2-cyclopentyl-6-methylaniline are diazotized according to Example 1, Paragraph a) and reacted with copper(I) chloride. Steam distillation gives 100.1 g of a crude product which, according to gas chromatographic analysis, consists of 56.4% of 2-chloro-3-cyclopentyltoluene and 32% of 2-chloro-3-cyclopentylphenol. The phenol is separated off according to Example 1, Paragraph a) and can be reacted again according to Paragraph (b). 60.4 g of 2-chloro-3-cyclopentyltoluene of boiling point 140° C./0.5 mbar are obtained.

e) Electrolytic synthesis of 2-chloro-3-cyclopentylbenzyl acetate

The 2-chloro-3-cyclopentyltoluene obtained according to Paragraph d) is electrolyzed in the electrolysis cell described below, under the stated conditions.

Apparatus: undivided cell having 11 bipolar electrodes.
Anode: graphite.
Electrolyte: 41 g (0.211 mole) of 2-chloro-3-cyclopentyltoluene, 350 g of acetic anhydride, 175 g of $KSO_3C_6H_5$ and 2,934 g of acetic acid.
Cathode: graphite
Current density: 1.33 A/dm$^2$.
Electrolysis temperature: 70°–75° C.
Electrolysis with 9 F/mole of 2-chloro-3-cyclopentyltoluene.

The electrolyte is pumped through the cell at a rate of 200 l/h during the electrolysis.

The discharged electrolysis mixture is worked up similarly to Example 1, Paragraph b. The residue (105 g) contains 7.0 g of 2-chloro-3-cyclopentyltoluene and 37.1 g of 2-chloro-3-cyclopentylbenzyl acetate according to gas chromatographic analysis. This gives a conversion of 82.8%, a yield of 69.6% and a selectivity of 84.1%. 2-Chloro-3-cyclopentylbenzyl acetate is purified by distillation at 140°–150° C. and under 4 mbar.

$^1$H—NMR (270 MHz, CDCl$_3$).

δ (ppm)=1.45–1.9 (m, 8H, cyclopentyl—CH$_2$); 2.1 (s, 3H, CH$_3$COO—); 3.5 (quintet, 1H, cyclopentyl—CH); 5.2 (s, 2H, —CH$_2$OAc); 7.2 (m, 3H, aromat.—H).

$^{13}$C—NMR (270 MHz, CDCl$_3$).

δ (ppm)=20.7 (q), 25.5 (t, 2C); 33.3 (t, 2C); 42.3 (d); 64.3 (t); 126.6 (d); 126.9 (d); 127.0 (d); 133.5 (s); 134.1 (s); 144.4 (s); 170.4 (s).

f) Preparation of 2-chloro-3-cyclopentylbenzyl alcohol 8.1 g of 2-chloro-3-cyclopentylbenzyl acetate are hydrolyzed similarly to Example 1, Paragraph c. 2-Chloro-3-cyclopentylbenzyl alcohol of boiling point 123°–125° C. (0.2 mbar) are obtained in a yield of 5.8 g (86%).

$^1$H—NMR (200 MHz, CDCl$_3$).

δ (ppm)=1.4–2.3 (m, 9H, cyclopentyl-CH$_2$ and —OH); 3.5 (m, 1H, —CH); 4.8 (s, 2H, CH$_2$—OH); 7.2–7.4 (m, 3H, aromat.—H).

EXAMPLE 3

2-Fluoro-3-isopropylbenzyl alcohol a) Preparation of 2-fluoro-3-isopropyltoluene 44.7 g (0.3 mole) of 2-methyl-6-isopropylaniline are added dropwise to 200 ml of 40% strength tetrafluoboric acid at 5° C., followed by a solution of 20.7 g of sodium nitrite in 20 ml of water. The mixture is stirred for 1 hour at 10° C. The precipitated diazonium tetrafluoborate is filtered off under suction and suspended in succession in 50 ml of ice water, 50 ml of cold ethanol and 50 ml of diethyl ether. The suspension is added dropwise to a flask preheated at 150° C. When the evolution of gas has ended, the product is obtained by distillation over a Claisen still (bath temperature 100° C., pressure 4 mbar, distillation temperature 41°–42° C.). 28 g (61%) of 2-fluoro-3-isopropyltoluene are obtained.

b) Electrolytic synthesis of 2-fluoro-3-isopropylbenzyl acetate

The 2-fluoro-3-isopropyltoluene obtained according to Paragraph a is electrolyzed in the electrolysis cell described below, under the stated conditions.

Apparatus: undivided cell having 11 bipolar electrodes
Anode: graphite.
Electrolyte: 131 g (0.862 mole) of 2-fluoro-3-isopropyltoluene, 350 g of acetic anhydride and 175 g of $KSO_3C_6H_5$.
Cathode: graphite.
Current density: 1.33 A/dm².
Electrolysis temperature: 70° C.
Electrolysis with 5 F/mole of 2-fluoro-3-isopropyltoluene.
The electrolysis is pumped through the cell at a rate of 200 l/h during the electrolysis.

The discharged electrolysis mixture is worked up similarly to Example 1, Paragraph b. The residue (324 g) contains 1.3 g of 2-fluoro-3-isopropyltoluene and 94.3 g of 2-fluoro-3-isopropylbenzyl acetate according to gas chromatographic analysis. This gives a conversion of 99%, a yield of 52.1% and a selectivity of 52.6%. 2-Fluoro-3-isopropylbenzyl acetate is purified by distillation at 74° C. and under 2 mbar.

$^1H$—NMR (270 MHz, $CDCl_3$).

δ (ppm)=1.25 (d, 6H, —CH($C\overline{H}_3$)₂); 2.1 (s, 3H, $CH_3COO$—); 3.26 (septet, 1H, —$C\overline{H}(CH_3)_2$); 5.18 (s, 2H, —$CH_2OAc$); 7.05–7.3 (m, 3H, aromat.—H).

c) Preparation of 2-fluoro-3-isopropylbenzyl alcohol 44 g of 8% strength sodium hydroxide solution are added to a solution of 15.3 g (73 millimoles) of 2-fluoro-3-isopropylbenzyl acetate in 100 ml of dioxane. After 5 hours at 50° C., the mixture is poured into 100 ml of water. 12 g (98%) of 2-fluoro-3-isopropylbenzyl alcohol are obtained by extraction with dichloromethane.

$^1H$—NMR (200 MHz, $CDCl_3$).

δ (ppm)=1.25 (d, 6H, —CH($CH_3$)₂; 2.13 (s, 1H, —OH); 3.26 (septet, 1H, —$CH(C\overline{H}_3)_2$); 4.75 (s, 2H, —$CH_2OH$); 7.05–7.29 (m, 3H, aromat.—H).

EXAMPLE 4

2-Bromo-3-isopropylbenzyl alcohol a) Preparation of 2-bromo-3-isopropyltoluene

2-Bromo-3-isopropyltoluene of boiling point 105°–110° C./10 mbar is obtained from 2-isopropyl-6-methylaniline similarly to Example 1, Paragraph a, by means of a Sandmeyer reaction with copper(I) bromide.

b) Electrolytic synthesis of 2-bromo-3-isopropylbenzyl acetate

The 2-bromo-3-isopropyltoluene obtained according to Paragraph a) is electrolyzed in the electrolysis cell described below, under the stated conditions.

Apparatus: undivided cell having 11 bipolar electrodes
Anode: graphite.
Electrolyte: 207 g (0.972 mole) of 2-bromo-3-isopropyltoluene, 350 g of acetic anhydride, 175 g of $KSO_3C_6H_5$ and 2,763 g of acetic acid.
Cathode: graphite.
Current density: 1.33 A/d².
Electrolysis temperature: 70°–75° C.
Electrolysis with 9 F/mole of 2-bromo-3-isopropyltoluene.
The electrolyte is pumped through the cell at a rate of 200 l/h during the electrolysis.

The discharged electrolysis mixture is worked up similarly to Example 1, Paragraph b. The residue (309 g) contains 26.3 g of 2-bromo-3-isopropyltoluene and 153.9 g of 2-bromo-3-isopropylbenzyl acetate according to gas chromatographic analysis. This gives a conversion of 87.3%, a yield of 58.4% and a selectivity of 66.9%. 2-Bromo-3-isopropylbenzyl acetate is purified by distillation at 130° C. and under 4 mbar.

$^1H$—NMR (270 MHz, $CDCl_3$).

δ (ppm)=1 23 (d, 6H, —CH($C\overline{H}_3$)₂); 2.1 (s, 3H, $CH_3COO$—); 3.47 (septet, 1H, —$C\overline{H}(CH_3)_2$); 5.2 (s, 2H, —$CH_2OAc$); 7.25 (m, 3H, aromat.—H).

$^{13}C$—NMR (270 MHz, $CDCl_3$).

δ (ppm)=20.7 (q); 22.9 (q, 2C); 33.0 (d); 66.7 (t); 125.2 (s); 126.4 (d); 127.2 (d); 127.4 (d); 135.8 (s); 148.1 (s); 170.3 (s).

c) Preparation of 2-bromo-3-isopropylbenzyl alcohol 116 g (0.43 mole) of 2-bromo-3-isopropylbenzyl acetate in 770 ml of dioxane and 255 g of 8% strength sodium hydroxide solution are hydrolyzed and worked up similarly to Example 1, Paragraph c. 98.2 g (quantitative) of 2-bromo-3-isopropylbenzyl alcohol of boiling point 110°–112° C./0.2 mbar are obtained.

$^1H$—NMR (300 MHz, $CDCl_3$):

δ (ppm)=1.25 (d, 6H, —CH($CH_3$)₂); 2.2 (s, 1H, OH); 3.48 (septet, 1H, —CH<); 4.75 (s, 2H, —$CH_2$—); 7.2–7.4 (m, 3H, aromat.—H).

EXAMPLE 5

2-Chloro-3-cyclohexylbenzyl alcohol a) Preparation of 2-cyclohexyl-6-methylaniline 63.1 g (0.52 mole) of 3-chlorocyclohexene are added dropwise at room temperature to 278.6 g (2.6 moles) of o-toluidine while stirring, and the mixture is then heated to 160° C. and kept at this temperature for 6 hours. After cooling, the mixture is taken up in dichloromethane and washed with sodium hydroxide solution. 76.2 g of a mixture of the two anilines (92% of 2-(cyclohexen-3-yl)-6-methylaniline and 4% of 4-(cyclohexen-3-yl)-2-methylaniline) are obtained from the organic phase after drying, evaporation and rectification.

223.3 g (1.15 moles) of the aniline mixture are dissolved in 2 l of ethanol and are hydrogenated using 10 g of palladium/carbon (10%) at room temperature and under 0.2 bar gauge pressure. Filtering off the catalyst and evaporating down the filtrate give 217 g of a crude product which consists of 92% of 2-cyclohexyl-6-methylaniline according to gas chromatography. By conversion to the hydrochloride and recrystallization from water/ethanol, 2-cyclohexyl-6-methylaniline is obtained in pure form as the hydrochloride. Mp.: 54°–55° C.

b) Preparation of 2-chloro-3-cyclohexyltoluene

2-Chloro-3-cyclohexyltoluene of boiling point 73°–75° C./0.1 mbar is obtained similarly to Example 1, Paragraph a), in a yield of 20%, from the 2-cyclohexyl-6-methylaniline prepared according to Paragraph a).

c) Electrolytic synthesis of 2-chloro-3-cyclohexylbenzyl acetate

The 2-chloro-3-cyclohexyltoluene obtained according to Paragraph b) is electrolyzed in the electrolysis cell described below, under the stated conditions.

Apparatus: undivided cell having 11 bipolar electrodes
Anode: graphite.
Electrolyte: 68 g (0.326 mole) of 2-chloro-3-cyclohexyltoluene, 350 g of acetic anhydride, 175 g of $KSO_3C_6H_5$ and 2,907 g of acetic acid.
Cathode: graphite.
Current density: 0.67 $A/dm^2$.
Electrolysis temperature: 70° C.
Electrolysis with 6 F/mole of 2-chloro-3-cyclohexyltoluene. The electrolyte is pumped through the cell at a rate of 200 l/h during the electrolysis.

The discharged electrolysis mixture is worked up similarly to Example 1, Paragraph b. After purification of the residue by distillation at 145°-165° C. and under 2 mbar, 0.9 g of 2-chloro-3-cyclohexyltoluene and 29.4 g of 2-chloro-3-cyclohexylbenzyl acetate are obtained. This gives a conversion of 98.7% and a yield of 33.7%.

$^1$H—NMR (270 MHz, $CDCl_3$).

δ (ppm)=1.2-1.5 (m, 5H, ring—H); 1.7-1.9 (m, 5H, ring—H); 2.1 (s, 3H, $CH_3COO$—); 3.06 (m, 1H, cyclohexyl—CH); 5.2 (s, 2H, —$CH_2OAc$); 7.2 (m, 3H, aromat.—H).

$^{13}$C—NMR (270 MHz, $CDCl_3$).

δ (ppm)=20.8 (q), 26.3 (t); 26.9 (t, 2C); 33.2 (t, 2C); 40.6 (d); 64.4 (t); 126.7, 127.0 (d, 3C); 132.8 (s); 133.9 (s); 145.4 (s); 170.5 (s).

d) Preparation of 2-chloro-3-cyclohexylbenzyl alcohol 26.4 g (99 millimoles) of 2-chloro-3-cyclohexylbenzyl acetate are added dropwise to a mixture of 150 ml of ethanol and 8.4 g (150 millimoles) of potassium hydroxide. After 6 hours at 50° C., the mixture is evaporated down under reduced pressure, water is added to the residue and the mixture is extracted with dichloromethane. After the organic phase has been worked up by a conventional method, it is subjected to fractional distillation under reduced pressure. 17.4 g (78%) of 2-chloro-3-cyclohexylbenzyl alcohol of boiling point 133°-135° C./0.5 mbar and $n_D^{20}$=1.5593 are obtained.

$^1$H—NMR (300 MHz, $CDCl_3$).

δ (ppm)=1.2-1.6 (m, 5H, cyclohexyl—H); 1.7-2.0 (m, 5H, cyclohexyl—H); 2.4 (s, 1H, OH); 3.1 (m, 1H, —CH<); 4.75 (s, 2H, —$CH_2OH$); 7.1-7.4 (m, 3H, aromat.—H).

EXAMPLE 6

3-Tert-butyl-2-chlorobenzyl alcohol a) Electrolytic synthesis of 3-tert-butyl-2-chlorobenzyl acetate

3-Tert-butyl-2-chlorotoluene prepared similarly to Example 1, Paragraph a) is electrolyzed in the electrolysis cell described below, under the stated conditions.

Apparatus: undivided cell having 11 bipolar electrodes.
Anode: graphite.
Electrolyte: 121 g (0.662 mole) of 3-tert-butyl-2-chlorotoluene [$^1$H—NMR (300 MHz, $CDCl_3$); δ (ppm)=1.5 (s, 9H); 2.2 (s, 3H); 7.0-7.4 (m, 3H)], 350 g of acetic anhydride, 175 g of $KSO_3C_6H_5$ and 2,854 g of acetic acid.
Cathode: graphite.
Current density: 1.33 $A/dm^2$.
Electrolysis temperature: 70° C.
Electrolysis with 4.5 F/mole of 3-tert-butyl-2-chlorotoluene.
The electrolyte is pumped through the cell at a rate of 200 l/h during the electrolysis.

The discharged electrolysis mixture is worked up similarly to Example 1, Paragraph b. The residue (205 g) contains 9.4 g of 3-tert-butyl-3-chlorotoluene and 107 g of 3-tert-butyl-2-chlorobenzyl acetate according to gas chromatographic analysis. This gives a conversion of 92.2%, a yield of 67.1% and a selectivity of 72.8%. 3-Tert-butyl-2-chlorobenzyl acetate is purified by distillation at 112° C. and under 2 mbar.

$^1$H—NMR (270 MHz, $CDCl_3$).

δ (ppm)=1.5 (s, 9H, —$C(CH_3)_3$); 2.1 (s, 3H, $CH_3COO$—); 5.2 (s, 2H, —$CH_2OAc$); 7.15 (t, 1H, aromat.—H); 7.25 (d, 1H, aromat.—H); 7.38 (d, 1H, aromat.—H).

$^{13}$C—NMR (270 MHz, $CDCl_3$).

δ (ppm)=20.6 (q); 29.9 (q, 3C); 36.4 (s); 64.6 (t); 126.4 (d); 127.2 (d); 127.5 d); 133.1 (s); 135.7 (s); 147.1 (s); 170.1 (s).

b) Preparation of 3-tert-butyl-2-chlorobenzyl alcohol 21.0 g (0.39 mole) of potassium hydroxide are added to a solution of 62.6 g (0.26 mole) of 3-tert-butyl-2-chlorobenzyl acetate in 400 ml of ethanol. The reaction mixture is stirred for 6 hours at 50° C. and evaporated and the residue is taken up with water. The aqueous mixture is extracted with dichloromethane. 51 g (quantitative) of 3-tert-butyl-2-chlorobenzyl alcohol of boiling point 103°-105° C./0.2 mbar are obtained from the organic phase.

EXAMPLE 7

3-Tert-butyl-2-fluorobenzyl alcohol a) Preparation of 3-tert-butyl-2-fluorotoluene 157 g (0.96 mole) of 2-tert-butyl-6-methylaniline are added dropwise to 500 ml of 40% strength tetrafluoroboric acid at 50° C., followed by a solution of 66.2 g (0.96 mole) of sodium nitrite in 270 ml of water. The mixture is stirred for 1 hour at 10° C. The precipitated diazonium salt is filtered off under suction, washed in succession with 50 ml of ice water, 50 ml of cold ethanol and 50 ml of diethyl ether and then suspended in 500 ml of liquid paraffin. The suspension is then added dropwise to a flask preheated at 150° C. After evolution of gas is ended, the product is obtained by distillation over a Claisen still (bath temperature 140° C., pressure 26 mbar) at a distillation temperature of 83° C. 47 g (29%) of 2-fluoro-3-tert-butyltoluene are obtained.

$^1$H—NMR ($CDCl_3$).

δ (ppm)=1.38 (s, 9H, $C(CH_3)_3$); 2.22 (s, 3H, Ar—$CH_3$); 6.82-6.98 (m, 2H, aromat.—H); 7.05-7.12 (m, 1H, aromat.—H).

b) Electrolytic synthesis of 3-tert-butyl-2-fluorobenzyl acetate

The 3-tert-butyl-2-fluorotoluene obtained according to Paragraph a) is electrolyzed in the electrolysis cell described below, under the stated conditions.

Apparatus: undivided cell having 11 bipolar electrodes.
Anode: graphite.

Electrolyte: 50 g (0.301 mole) of 3-tert-butyl-2-fluorotoluene, 300 g of acetic anhydride, 150 g of $KSO_3C_6H_5$ and 2,600 g of acetic acid.

Cathode: graphite.

Current density: 0.67 $A/dm^2$.

Electrolysis temperature: 70° C.

Electrolysis with 5 F/mole of 3-tert-butyl-2-fluorotoluene.

The electrolyte is pumped through the cell at a rate of 200 l/h during the electrolysis.

The discharged electrolysis mixture is worked up similarly to Example 1, Paragraph b). The residue (110 g) contains 1.3 g of 3-tert-butyl-2-fluorotoluene and 45.9 g of 3-tert-butyl-2-fluorobenzyl acetate according to gas chromatographic analysis. This gives a conversion of 97.4%, a yield of 68.3% and a selectivity of 69.9%.

3-Tert-butyl-2-fluorobenzyl acetate is purified by distillation at 105° C. and under 4 mbar.

$^1H$—NMR (270 MHz, $CDCl_3$)

δ (ppm)=1.38 (s, 9H, —C($CH_3$)$_3$); 2.05 (s, 3H, $CH_3COO$—); 5.18 (s, 2H, —$CH_2OAc$); 7.0 (t, 1H, aromat.—H), 7.22 (m, 2H, aromat.—H).

$^{13}C$—NMR (270 MHz, $CDCl_3$).

δ (ppm)=20.7 (q); 30.1 (q, 3C); 60.4 (t); 123.6 (d); 124.2 (s); 127.5 (d); 128.2 (d); 137.4 (s); 160.3 (s); 170.4 (s).

C) Preparation of 3-tert-butyl-2-fluorobenzyl alcohol 67 g of 8% strength aqueous sodium hydroxide solution are added to a solution of 25 g (0.11 mole) of 3-tert-butyl-2-fluorobenzyl acetate in 100 ml of dioxane and the mixture is stirred for 7 hours at 50° C., diluted with 100 ml of water and extracted three times with dichloromethane. Drying and evaporation give 19.5 g (97%) of 3-tert-butyl-2-fluorobenzyl alcohol.

$^1H$—NMR ($CDCl_3$)

δ (ppm)=1.38 (s, 9H, C($CH_3$)$_3$); 2.21 (s, 1H, —OH); 4.71 (s, 2H, —$CH_2$—); 7.00–7.09 (m, 1H, aromat.—H); 7.18–7.30 (m, 2H, aromat.—H).

EXAMPLE 8

2-Chloro-3-methylbenzyl alcohol a) Electrolytic synthesis of 2-chloro-3-methylbenzyl acetate 2-Chloro-1,3-dimethylbenzene is electrolyzed in the electrolysis cell described below, under the stated conditions.

Apparatus: undivided cell having 11 bipolar electrodes.

Anode: graphite.

Electrolyte: 115 (0.819 mole) of 2-chloro-1,3-dimethylbenzene, 350 g of acetic anhydride, 175 g of $KSO_3C_6H_5$ and 2,860 g of acetic acid.

Cathode: graphite.

Current density: 0.67 $A/dm^2$.

Electrolysis temperature: 70° C.

Electrolysis with 4.5 F/mole of 2-chloro-1,3-dimethylbenzene.

The electrolyte is pumped through the cell at a rate of 200 l/h during the electrolysis.

The discharged electrolysis mixture is worked up similarly to Example 1, Paragraph b). The residue (200 g) contains 0.8 g of 2-chloro-1,3-dimethylbenzene and 77 g of 2-chloro-3-methylbenzyl acetate according to gas chromatographic analysis. This gives a conversion of 99.3%, a yield of 47.4% and a selectivity of 47.7%.

2-Chloro-3-methylbenzyl acetate is purified by distillation at 87°–90° C. and under 2 mbar.

$^1H$—NMR (270 MHz, $CDCl_3$).

δ (ppm)=2.08 (s, 3H, $CH_3COO$—); 2.35 (s, 3H, $CH_3$—Ar); 5.2 (s, 2H, —$CH_2OAc$); 7.05–7.22 (m, 3H, aromat.—H).

$^{13}C$—NMR (270 MHz, $CDCl_3$).

δ (ppm)=20.3 (q,); 20.8 (q); 64.0 (t); 126.3 (d); 127.1 (d); 130.6 (d); 133.6 (s); 133.8 (s); 136.6 (s); 170.4 (s).

b) Preparation of 2-chloro-3-methylbenzyl alcohol 68 g (0.34 mole) of the benzyl acetate obtained according to Paragraph a), in a mixture of 640 ml of dioxane and 65 ml of 10% strength sodium hydroxide solution, are hydrolyzed and worked up similarly to Example 1, Paragraph c). 43 g (81%) of 2-chloro-3-methylbenzyl alcohol of melting point 63°–64° C. are obtained.

EXAMPLE 9

Electrolytic synthesis of 2-chloro-3-isopropyl-benzyl propionate

2-Chloro-3-isopropyltoluene is electrolyzed in the electrolysis cell described below, under the stated conditions.

Apparatus: undivided cell having 11 bipolar electrodes.

Anode: graphite.

Electrolyte: 242 g (1.436 moles) of 2-chloro-3-isopropyltoluene, 125 g of ($Et_3NMe$)$SO_4Me$ and 2,133 g of propionic acid.

Cathode: graphite.

Current density: 0.67 $A/dm^2$.

Electrolysis temperature: 70° C.

Electrolysis with 8 F/mole of 2-chloro-3-isopropyltoluene.

The electrolyte is pumped through the cell at a rate of 200 l/h during the electrolysis.

The discharged electrolysis mixture is worked up similarly to Example 1, Paragraph b. The residue (200 g) contains 9.2 g of 2-chloro-3-isopropyltoluene and 156.2 g of 2-chloro-3-isopropylbenzyl propionate according to gas chromatographic analysis. This gives a conversion of 96.2%, a yield of 47.0% and a selectivity of 48.9%. 2-Chloro-3-isopropylbenzyl propionate is purified by distillation at 117° C. and under 2 mbar.

1H—NMR (270 Hz, $CDCl_3$).

δ (ppm)=1.16 (t, 3H, $CH_3CH_2COO$—); 1.22 (d, 6H, —CH($CH_3$)$_2$); 2.37 (q, 2H, $CH_3CH_2COO$—); 3.45 (septet, 1H, —CH($CH_3$)$_2$), 5.2 (s, 2H, $ArCH_2O$—); 7.2 (m. 3H. aromat.—H).

$^{13}C$—NMR (270 MHz, $CDCl_3$).

δ (ppm)=9.1 (q); 22.7 (q, 2C); 27.6 (t); 30.3 (d); 64.1 (t); 126.4 (d); 126.8 (d); 127.0 (d); 132.8 (s); 134.4 (s); 146.5 (s); 173.7 (s).

EXAMPLE 10

Electrolytic synthesis of 2-chloro-3-isopropylbenzyl formate

2-Chloro-3-isopropyltoluene is electrolyzed in the electrolysis cell described below, under the stated conditions.

Apparatus: undivided cell having 11 bipolar electrodes.

Anode: graphite.

Electrolyte: 250 g (1.484 moles) of 2-chloro-3-isopropyltoluene, 1,400 g of acetonitrile, 125 g of ($Et_3NMe$)-$SO_4Me$ and 2,125 g of formic acid.

Cathode: graphite.
Current density: 1.33 A/dm$^2$.
Electrolysis temperature: 70° C.
Electrolysis with 16 F/mole of 2-chloro-3-isopropyltoluene.

The electrolyte is pumped through the cell at a rate of 200 l/h during the electrolysis.

The discharged electrolysis mixture is worked up similarly to Example 1, Paragraph b. The residue (291 g) contains 128.3 g of 2-chloro-3-isopropyltoluene and 96.0 g of 2-chloro-3-isopropylbenzyl formate according to gas chromatographic analysis. This gives a conversion of 48.7%, a yield of 30.4% and a selectivity of 62.4%. 2-Chloro-3-isopropylbenzyl formate is purified by distillation at 103°–107° C. and under 2 mbar.

$^1$H—NMR (270 MHz, CDCl$_3$).

δ (ppm)=1.2 (d, 6H, —CH(C$\underline{H}$$_3$)$_2$); 3.45 (septet, 1H, —C$\underline{H}$(CH$_3$)$_2$); 5.27 (s, 2H, —C$\underline{H}$$_2$OCHO); 7.2 (m, 3, aromat.—H); 8.06 (s, 1H, —OCHO).

$^{13}$C—NMR (270 MHz, CDCl$_3$).

δ (ppm)=22.6 (q, 2C); 30.3 (d); 63.7 (t); 126.7 (d); 126.9 (d); 127.4 (d); 132.9 (s); 133.5 (s); 146.6 (s); 160.5 (d).

We claim:

1. A benzene derivative of the formula

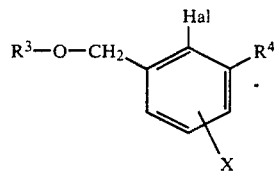

V where Hal is fluorine, chlorine or bromine, R$^4$ is a cyclic alkyl radical of 3 to 12 carbon atoms, R$^3$ is hydrogen or an R$^2$—CO—radical, R$^2$ is hydrogen or alkyl of 1 to 6 carbon atoms and X is hydrogen or halogen.

* * * * *